US009668303B2

(12) United States Patent
Augustine et al.

(10) Patent No.: US 9,668,303 B2
(45) Date of Patent: May 30, 2017

(54) FLEXIBLE ELECTRIC HEATERS

(71) Applicant: Augustine Biomedical and Design, LLC, Eden Prairie, MN (US)

(72) Inventors: Scott D. Augustine, Deephaven, MN (US); Randall C. Arnold, Minnetonka, MN (US); Rudolf Andreas Deibel, Eden Prairie, MN (US); Scott A. Entenman, St. Paul, MN (US)

(73) Assignee: Augustine Biomedical and Design, LLC, Eden Prairie, MN (US)

( * ) Notice: Subject to any disclaimer, the term of this patent is extended or adjusted under 35 U.S.C. 154(b) by 2 days.

(21) Appl. No.: 14/255,933

(22) Filed: Apr. 17, 2014

(65) Prior Publication Data

US 2014/0312027 A1    Oct. 23, 2014

Related U.S. Application Data

(60) Provisional application No. 61/812,987, filed on Apr. 17, 2013.

(51) Int. Cl.
*H05B 1/02* (2006.01)
*H05B 3/34* (2006.01)
(Continued)

(52) U.S. Cl.
CPC .......... *H05B 3/342* (2013.01); *A47C 21/048* (2013.01); *A61F 7/007* (2013.01); *A61F 7/0097* (2013.01); *A61F 7/08* (2013.01); *A61G 13/10* (2013.01); *B32B 27/12* (2013.01); *H05B 3/12* (2013.01); *H05B 3/145* (2013.01); *H05B 3/146* (2013.01);
(Continued)

(58) Field of Classification Search
CPC .... H05B 3/342; H05B 2203/036; H05B 3/12; H05B 3/145; H05B 3/146; B32B 27/12; A61F 7/0097; A61F 7/08; A61F 2007/0098; A47C 21/008; A61G 13/10
USPC ....... 219/481, 212, 505, 494, 528, 529, 544, 219/549; 428/201
See application file for complete search history.

(56) References Cited

U.S. PATENT DOCUMENTS

| 2,715,674 A | 8/1955 | Abbott et al. |
| 3,582,456 A * | 6/1971 | Stolki ..................... B32B 27/00 428/215 |

(Continued)

FOREIGN PATENT DOCUMENTS

| WO | 9923992 A1 | 5/1999 |
| WO | 0195841 A2 | 12/2001 |

(Continued)

OTHER PUBLICATIONS

European Patent Application No. 12757173.5, Supplementary European Search Report mailed Jun. 1, 2015, 9 pages.

*Primary Examiner* — Mark Paschall
(74) *Attorney, Agent, or Firm* — Fredrikson & Byron, P.A.

(57) ABSTRACT

Embodiments include a flexible fabric heater. The fabric heater has a conductive base fabric having elastic properties. The base fabric may be coupled to electrical terminals. A elastomeric layer may be applied on the base fabric. The elastomeric layer may have elastic properties and includes a liquid-resistant material. A first thermal layer may be applied proximate edges along the electrical coupling between the fabric heater and the electrical terminals. The first thermal layer can have heat-resistant properties.

20 Claims, 2 Drawing Sheets

(51) Int. Cl.
*A61F 7/00* (2006.01)
*A47C 21/04* (2006.01)
*A61F 7/08* (2006.01)
*A61G 13/10* (2006.01)
*H05B 3/12* (2006.01)
*H05B 3/14* (2006.01)
*B32B 27/12* (2006.01)
*A61G 13/12* (2006.01)

(52) U.S. Cl.
CPC ...... *H05B 3/347* (2013.01); *A61F 2007/0071* (2013.01); *A61F 2007/0095* (2013.01); *A61F 2007/0098* (2013.01); *A61G 13/126* (2013.01); *A61G 2210/90* (2013.01); *B32B 2274/00* (2013.01); *B32B 2307/202* (2013.01); *B32B 2307/7265* (2013.01); *B32B 2439/00* (2013.01); *H05B 2203/013* (2013.01); *H05B 2203/016* (2013.01); *H05B 2203/029* (2013.01); *H05B 2203/036* (2013.01)

(56) References Cited

U.S. PATENT DOCUMENTS

| | | |
|---|---|---|
| 3,780,262 A | 12/1973 | Rudd |
| 3,808,403 A | 4/1974 | Kanaya et al. |
| 4,423,308 A | 12/1983 | Callaway et al. |
| 4,495,402 A | 1/1985 | Burdick et al. |
| 4,941,961 A * | 7/1990 | Noguchi ............... C25D 17/10 204/280 |
| 5,023,433 A | 6/1991 | Gordon et al. |
| 5,320,164 A | 6/1994 | Szczesuil et al. |
| 5,723,845 A | 3/1998 | Partington et al. |
| 5,755,275 A | 5/1998 | Rose et al. |
| 5,835,983 A | 11/1998 | McMahen et al. |
| 5,881,410 A | 3/1999 | Yamada |
| 5,932,129 A | 8/1999 | Hyatt et al. |
| 6,038,722 A | 3/2000 | Giori et al. |
| 6,084,217 A | 7/2000 | Bulgajewski et al. |
| 6,189,487 B1 | 2/2001 | Owen et al. |
| 6,210,427 B1 | 4/2001 | Augustine et al. |
| 6,215,111 B1 | 4/2001 | Rock et al. |
| 6,229,123 B1 | 5/2001 | Kochman et al. |
| 6,240,623 B1 | 6/2001 | Johansson et al. |
| 6,373,034 B1 | 4/2002 | Rock et al. |
| 6,403,935 B2 | 6/2002 | Kochman et al. |
| 6,416,534 B1 | 7/2002 | Montagnino et al. |
| 6,434,328 B2 | 8/2002 | Rutherford |
| 6,452,138 B1 | 9/2002 | Kochman et al. |
| 6,452,139 B1 | 9/2002 | Benoit et al. |
| 6,582,456 B1 | 6/2003 | Hand et al. |
| 6,770,854 B1 | 8/2004 | Keane |
| 6,872,758 B2 | 3/2005 | Simpson et al. |
| 6,933,469 B2 | 8/2005 | Ellis et al. |
| 6,967,309 B2 | 11/2005 | Wyatt et al. |
| 7,053,344 B1 | 5/2006 | Surjan et al. |
| 7,161,120 B1 | 1/2007 | Stroud et al. |
| 7,176,419 B2 | 2/2007 | Ellis et al. |
| 7,375,308 B2 * | 5/2008 | Ferguson ............... 219/549 |
| 7,543,344 B2 | 6/2009 | Augustine et al. |
| 7,714,255 B2 | 5/2010 | Augustine et al. |
| 7,851,729 B2 | 12/2010 | Augustine et al. |
| 8,065,763 B2 | 11/2011 | Brykalski et al. |
| 8,283,602 B2 | 10/2012 | Augustine et al. |
| 8,288,693 B2 | 10/2012 | Weiss et al. |
| 8,291,612 B2 * | 10/2012 | Ferguson ............... 36/2.6 |
| 8,418,297 B2 | 4/2013 | Mikkelsen et al. |
| 8,624,164 B2 | 1/2014 | Deibel et al. |
| 8,698,044 B2 | 4/2014 | Burr et al. |
| 2001/0020303 A1 | 9/2001 | Endo et al. |
| 2002/0124312 A1 | 9/2002 | Yoon |
| 2004/0149711 A1 | 8/2004 | Wyatt et al. |
| 2004/0164499 A1 | 8/2004 | Murakami et al. |
| 2004/0174056 A1 | 9/2004 | Gryp et al. |
| 2004/0237206 A1 | 12/2004 | Webster et al. |
| 2005/0016982 A1 | 1/2005 | Campf et al. |
| 2006/0260060 A1 | 11/2006 | Apperson et al. |
| 2006/0261055 A1 | 11/2006 | Child et al. |
| 2007/0068930 A1 | 3/2007 | Augustine et al. |
| 2007/0108190 A1 | 5/2007 | Ferguson |
| 2007/0152479 A1 | 7/2007 | Howman et al. |
| 2007/0164010 A1 | 7/2007 | Rock et al. |
| 2007/0272673 A1 | 11/2007 | Keane |
| 2008/0173629 A1 | 7/2008 | Deibel et al. |
| 2008/0255641 A1 | 10/2008 | Ellis |
| 2008/0283513 A1 | 11/2008 | Ferguson, III et al. |
| 2009/0078690 A1 | 3/2009 | Lee et al. |
| 2009/0095735 A1 | 4/2009 | Resheff |
| 2009/0099631 A1 * | 4/2009 | Augustine et al. ........... 607/104 |
| 2009/0222996 A1 | 9/2009 | Balonick et al. |
| 2010/0078807 A1 | 4/2010 | Schulz |
| 2010/0119704 A1 | 5/2010 | Hemmelgarn et al. |
| 2010/0161016 A1 | 6/2010 | Augustine et al. |
| 2010/0200558 A1 | 8/2010 | Liu et al. |
| 2010/0204763 A1 | 8/2010 | Augustine et al. |
| 2010/0224612 A1 | 9/2010 | Asami et al. |
| 2010/0279086 A1 * | 11/2010 | Park et al. ................ 428/201 |
| 2010/0283295 A1 | 11/2010 | Smith et al. |
| 2010/0325796 A1 | 12/2010 | Lachenbruch et al. |
| 2011/0031230 A1 | 2/2011 | Kim |
| 2012/0111846 A1 | 5/2012 | Hammerschmidt |
| 2012/0273475 A1 | 11/2012 | An |
| 2012/0279953 A1 * | 11/2012 | Augustine et al. ........... 219/217 |
| 2014/0074086 A1 | 3/2014 | MacIntyre-Ellis et al. |

FOREIGN PATENT DOCUMENTS

| | | |
|---|---|---|
| WO | 2007041389 A1 | 4/2007 |
| WO | 2010107724 A1 | 9/2010 |

* cited by examiner

FLEXIBLE ELECTRIC HEATERS

PRIORITY

This application claims priority to U.S. Provisional Application No. 61/812,987, Flexible Electric Heaters, filed on Apr. 17, 2013, the disclosure of which is hereby incorporated by reference in the entirety.

FIELD

This disclosure generally relates to systems and methods for electric heaters. More particularly, this disclosure relates to systems and methods for protective liquid-resistant fabric electric heaters.

BACKGROUND

Electrical resistance heaters made from flexible electrically conductive fabrics are known in the art. Such heaters include heated blankets, heated clothing, heated car seats and the like. The electrically conductive elements in such heaters are made from carbon fibers, thin metal wires or foil. The carbon fibers or metal wires are formed into bundles and then woven into a mesh-like cloth or simply anchored to a backing material by sewing and/or sealing (e.g., by a potting material such as rubber). Electrical connections (e.g., via a bus bar) are usually coupled to opposite ends of the conductive cloth or conductive bundle.

The carbon fiber bundles and/or metal wires forming heater elements of this construction are typically flexible. Embodiments including carbon fiber bundles, for instance, retain mechanical properties at very high temperature (e.g., 1000 degree Celsius). However, while masses of carbon fibers potted in resin may be one of the strongest materials known, individual carbon fibers that are not potted in resin are easily fractured when they are flexed. Various manufacturers have developed a variety of ways of attempting to make carbon fibers more tolerant of flexing but the result is still a bundle of relatively fragile fibers that eventually fracture with repeated flexion and mechanical stress. The point of repeated flexion and stress is usually where the fabric heater is folded or bent. For instance, in the case of a heater for a car seat, the areas of the seat that maximally deflect are those that are subject to repetitive placement of a weight (e.g., a user's body).

When fiber bundle, resistance wires or foil heater elements develop repetitive mechanical stress, it may result in arcing due to a local region of higher resistance. For instance, if individual carbon fibers fracture in a given area, the electrical resistance increases in that area. This increase in resistance may either be gradual over time, or develop rapidly in the case of an acute fracture. As electrical currents preferentially follow the path of least resistance, the current may bypass the fractured area of higher resistance and flow via adjacent bundles. Thus, the area adjacent the fractured area develops higher current flow as the fracture evolves. This excess electrical current flow may result in excess heat being produced adjacent the fractured heater bundles, thereby creating localized areas of higher temperature (e.g., a hotspot) adjacent the fractured area.

As more and more fibers fracture, more and more electrical current is routed through the remaining conducting bundles of fibers. These bundles can become hot enough to burn (e.g., through a car seat) and sometimes cause discomfort or injury to a user (e.g., the occupant of the car seat). Such embodiments may develop hotspots in regions of maximum flexion or mechanical stress, which typically correlates with the point of contact between the user and the fabric heater (e.g., the point of contact between the occupant and the car seat). Thus, hotspots may develop in those areas where it is likely to contact the user and cause burn injuries.

In order to mitigate hotspot development in flexible heaters, fabric heater elements may be protected by providing a laminate. The laminate may include two or more layers of plastic film, woven or non-woven fabric, potting material such as silicone or a combination of these materials. The laminate may add mechanical strength to fabric heater to prevent fracture of fabric heater elements, and may provide both electrical insulation (especially via potting materials) and moisture protection to the heating element. However, the resulting heater may lose flexibility and elasticity, thereby preventing the fabric heater from being formed or disposed into complex shapes (e.g., a compound curve bending in two directions simultaneously). Such a heater construction with reduced flexibility and minimal elasticity may limit the usefulness of these heaters in applications such as warming blankets, warming mattresses and warmed clothing.

SUMMARY OF THE INVENTION

Certain embodiments include a fabric heater. The fabric heater may include a base fabric having elastic properties. The base fabric can deform when a load is applied on the fabric heater. A first electrical terminal can be electrically coupled to the base fabric proximate a first edge and a second electrical terminal can be electrically coupled to the base fabric proximate a second edge opposite the first edge. An elastomeric layer may be applied on at least one surface of the base fabric. The elastomeric layer may have elastic properties thereby allowing the fabric heater to deform. The elastomeric layer may include liquid-resistant properties thereby preventing a liquid from contacting at least one of the first and second faces, on which the elastomeric layer is applied.

In some embodiments the elastomeric layer can be applied on the base fabric of the fabric heater such that the elastomeric layer substantially covers an entire surface of the base fabric extending into proximity with the first and second electrical terminal. In such embodiments, the elastomeric layer may be disposed at a distance less than or equal to approximately 0.1 inches from the first electrical terminal, and at a distance less than or equal to approximately 0.1 inches from the second electrical terminal. In some embodiments, the elastomeric layer may include an elastomer. In other embodiments, the elastomeric layer may include a polymer film. In some embodiments, the elastomeric layer may substantially enclose the fabric heater, including the electrical terminals.

In some embodiments, a first thermal layer can be applied proximate the first edge and the second edge, of the base fabric. The first thermal layer may cover the electrical coupling between the fabric heater and the first and second electrical terminals and may have heat-resistant properties. In some embodiments, the fabric heater may be made of a material having a melting point lower than its ignition temperature for burning. The first thermal layer may be an elastomeric coating. The first thermal layer may be a thermoplastic elastomeric coating. The elastomer or thermoplastic elastomer forming the first thermal layer may have heat resistant properties.

The details of one or more embodiments of the invention are set forth in the accompanying drawings and the description below. Other features, objects, and advantages will be apparent from the description and drawings, and from the claims.

BRIEF DESCRIPTION OF THE DRAWINGS

The following drawings are illustrative of particular embodiments of the present invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

DETAILED DESCRIPTION

Figure 1:
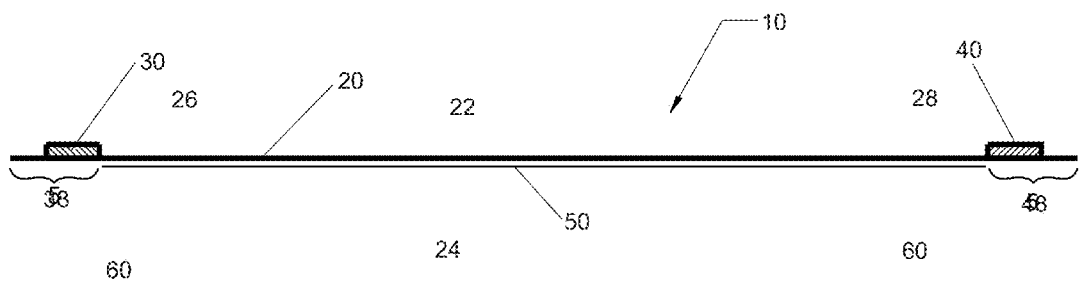
FIG. 1 is a front view of a fabric heater according to a first embodiment with a elastomeric layer applied on the bottom face of the fabric heater.

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention include a fabric heater. Such embodiments may be used in heated blankets, heated mattresses and similar body warming systems typically used for medical applications (e.g., in surgery), or consumer body warming systems such as car seats, heated blankets, heated pads or heated clothing. For instance, certain embodiments of the invention can be incorporated into the heated mattress inventions disclosed in U.S. patent application Ser. No. 13/422,279. Embodiments of the invention described herein may be further understood by reference to U.S. Pat. No. 7,714,255, Bus Bar Attachments for Flexible Heating Elements, U.S. patent application Ser. No. 13/422,279, Heated Under-body Warming Systems, U.S. Pat. No. 8,283,602, Heating Blanket, the disclosures of each of which is hereby incorporated by reference in their entirety.

Fabric heaters according to certain embodiments includes durable electrically conductive or semi-conductive material coated or polymerized onto a carrier material such as woven or non-woven fabric. The resulting structure is flexible and may be elastic (e.g., stretchable under tension), resistant to mechanical damage and electrically conductive. When coupled to electrical terminals, the fabric heater acts like a resistor and provides heat due to resistive heating. The conductive and semi-conductive materials used in the fabric heater may exhibit varying degrees of chemical stability, resistance to oxidation, resistance to moisture and resistance to certain other chemicals. For example, semi-conductive polymers (e.g., polypyrrole) are very durable and resistant to mechanical damage and are relatively stable in dry air but degrade at a much faster rate in contact with water and urine. Certain oxidizing chemicals such hydrogen peroxide can destroy the electrical conductivity of polypyrrole almost instantly. To prevent degradation of electrical conductivity of the fabric heater, an elastomeric liquid-proof layer may be applied on the heater. The combination of a durable electrically conductive fabric and an elastomeric liquid-proof layer covering fabric heater material prevents local degradation of the fabric heater, creates a heater that may be resistant to failure across the surface area that is in contact with the user.

While the liquid-proof elastomeric coating may provide short-term protection against liquid exposure, prolonged exposure to liquids may damage even a heater that has an elastomeric layer coating and can cause accidental burn injury to the user. Alternatively, or in addition to damage by liquids, the fabric heater may develop mechanical stress, especially near the edges of the fabric heater, where the fabric heater contacts electrical terminals. Other types of failure such as failure of the electrical coupling between the fabric heater and the electrical terminals can also occur. Thus, in accordance with certain embodiments of the invention, where the edges of the fabric heaters electrically couple to one or more electrical terminals may be designed to fail in a controlled way, along the electrical terminal in order to stop current flow to the damaged surface of the fabric heater in the event of a prolonged liquid exposure. Interrupting current flow at the edges of a damaged fabric heater and away from the surface of the fabric heater that contacts a user may be beneficial in preventing the user from burn injuries. Certain embodiments may also include a coating applied along the edges of the fabric that are in electrical contact with electrical terminals. The coating may have heat-resistant properties (e.g., low thermal conductivity) and thermally insulate the user from the edges of contact between the electrical terminals and the fabric heater. In certain embodiments, the coating may be applied on the electrical terminals as well, thereby preventing the user from being exposed to excess heat from a damaged heater failing along the electrical terminal.

FIGS. 1-6 illustrate fabric heaters according various embodiments. The fabric heater 10 may have elastic properties, allowing the fabric heater to deform elastically when a load is applied on the fabric heater. A single layer of woven or non-woven polymeric base fabric 20 may provide mechanical strength for the fabric heater 10. The base fabric 20 can be chosen for its strength as well as the desired elastic properties (e.g., stretching, compressing, twisting etc.). For example, a woven twill fabric may be used if stretching in a single direction is adequate. Alternately, a knit fabric may be used if stretching in two directions is desirable. The base fabric 20 may include a material having a melting point lower than its ignition temperature for burning.

The base fabric 20 may be coated with a conductive or a semi-conductive material (not shown). When an electrical current is passed through the base fabric 20, the conductive or semi-conductive material acts as a resistor and generate heat. The electrically conductive or semi-conductive material may be applied directly to the chosen fabric (as a coating). In some embodiments, the electrically conductive material may be a semi-conductive polymer such as polypyrrole, which may be polymerized directly onto the individual fibers of the base fabric 20. Such semi-conductive fabrics may have an electrical resistance of approximately 10-100 ohms on the square. Alternatively, the electrically conductive material may be modified aniline compounds or carbon or metal impregnated inks that are coated or polymerized onto the base fabric 20. Other conductive and semi-conductive coatings are also within the scope of the invention.

As seen in FIGS. 1-6, the fabric heater 10 includes a first face 22, and a second face 24 opposite the first face 22. The first and second faces 22, 24 may extend between the first and second edges 26, 28 in proximity to the edges of the fabric heater. The fabric heater 10 may include a first electrical terminal 30 electrically coupled to the base 20. The first electrical terminal 30 may be positioned proximate the first edge 26 and extends along the first edge 26 from the first end to a second end, wherein the first and second ends may be spaced apart by the length of the electrical terminal 30 (extending along the viewing direction of FIGS. 1-6). A second electrical terminal 40 may be electrically coupled to the base fabric 20 proximate a second edge 28 opposite the first edge 26. The second electrical terminal 40 extends along the second edge 28 from the first end to the second end. In some embodiments, one or more stitches electrically couple the first and second electrical terminals 30, 40 to the base fabric 20. The stitches may be made with electrically conductive thread. The stiches may form a first seam 60 and a second seam 60 at the first and second edges 26, 28. In the illustrated embodiments, the first and second electrical terminals 30, 40 are bus bars. Other first and second electrical terminals 30, 40, such as crimp-on connectors, posts, electrical boards etc. may also be used instead of bus bars. While an exemplary embodiment involving electrically stitched bus bars are illustrated, the first and second electrical terminals 30, 40 may be coupled to the base fabric 20 by any known methods, such as using electrically conductive tape, by crimping the fabric to the electrical terminal etc.

The base fabric 20 may be of a durable construction and tolerant of repeated load application (e.g., via a user's body), and may undergo repetitive flexing without undue mechanical stresses developing on the base fabric 20. The base fabric 20 may have elastic properties (e.g., modulus of elasticity, dynamic modulus, etc.) that facilitate repetitive flexing of the fabric. The fabric heater 10 may be protected from moisture and/or electrically insulated from the user to comply with safe operation of the heater. To this end, a elastomeric layer 50 may be applied to the base fabric 20. In some embodiments, the elastomeric layer 50 may be applied after the base fabric 20 is coated with an electrically conductive or semi-conductive layer and sewn to the first and second electrical terminals 30, 40.

Figure 2:
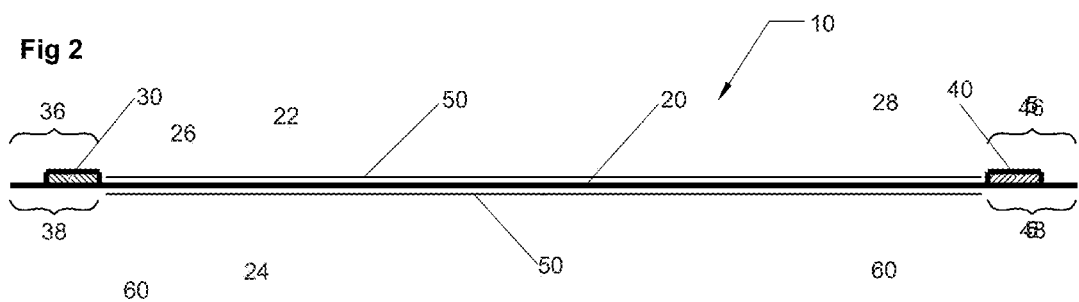
FIG. 2 is a front view of the fabric heater of FIG. 1 with a elastomeric layer applied on top and bottom faces of the fabric heater.

As seen in FIGS. 1-6, the elastomeric layer 50 substantially covers an entire surface of at least one of the first and second faces 22, 24 in proximity to the first and second electrical terminals 30, 40. As seen in FIG. 1, the elastomeric layer 50 may be applied on least one of the first and second faces 22, 24 of the fabric heater 10. For instance, as shown in FIG. 1, the elastomeric layer 50 is applied on the first face 22. As seen in FIG. 2, the elastomeric layer 50 is applied on both the first and second faces 22, 24. In such embodiments, the elastomeric layer 50 may have a elastomeric layer 50 end and a second layer end. The elastomeric layer 50 end may be disposed at a distance less than or equal to approximately 1 inch from the first electrical terminal 30. The second layer end may be disposed at a distance less than or equal to approximately 1 inch from the second electrical terminal 40. The elastomeric layer 50 end may be disposed at a distance less than or equal to approximately 0.1 inch from the first electrical terminal 30. The second layer end may be disposed at a distance less than or equal to approximately 0.1 inch from the second electrical terminal 40.

Figure 3:
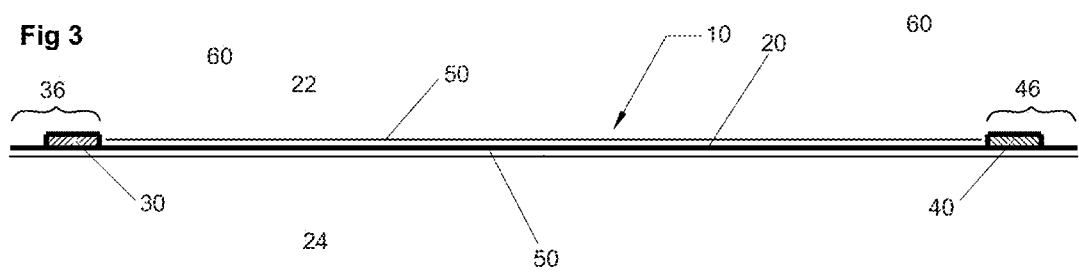
FIG. 3 is a front view of the fabric heater of FIG. 1, with the elastomeric layer applied on the top and bottom faces of the fabric heater, and on the bottom faces of the electrical terminals.
Figure 4:
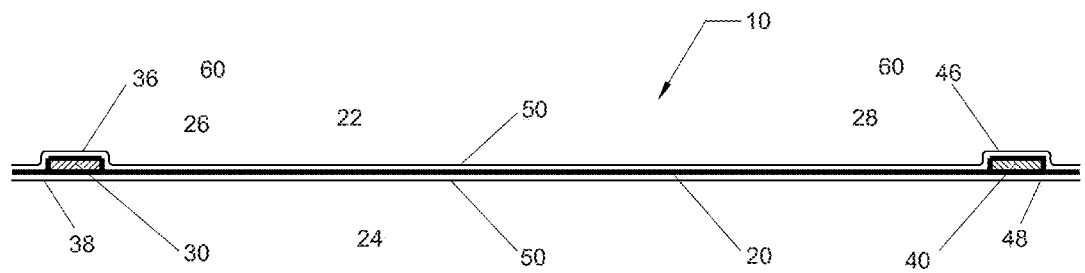
FIG. 4 is a front view of the fabric heater of FIG. 1, with the elastomeric layer applied on the top and bottom faces of the fabric heater, and on the top and bottom faces of the electrical terminals.

In alternate embodiments best seen in FIGS. 3 and 4, the elastomeric layer 50 can be applied on a first face 36 and/or a second face 38 of the first electrical terminal 30. In addition, the elastomeric layer 50 can be further applied on a first face 46 and/or a second face 48 of the second electrical terminal 40. When the elastomeric layer 50 is applied to both the first and second faces 22, 24 of the fabric heater 10, and also applied to the first and second faces 36, 46 and 38, 48 of the first and second electrical terminals 30, 40, the resulting heater may be substantially liquid-proof and chemical resistant and may prevent any liquid spill (e.g., water or coffee spills on a car seat) from contacting base fabric 20.

The elastomeric layer 50 may have properties that allow the fabric heater 10 to deform elastically (e.g., stretch). In some embodiments, the elastomeric layer 50 may have a thickness that is substantially less than the thickness of the fabric heater 10. For instance, the elastomeric layer 50 may have a thickness of less than about 0.01 inches (10 mils), to preserve the flexibility and stretchability of the base fabric 20. In addition, the elastomeric layer 50 may have elastic properties thereby allowing fabric heater 10 to stretch and deform when a load is applied to the fabric heater 10. An elastomeric layer of up to 0.05 inches (50 mils) is anticipated.

In some embodiments, the elastomeric layer 50 may include elastomers. Elastomers are a broad category of elastic polymer materials that includes but is not limited to: polyisoprene, polychloroprene (Neoprene), isobutylene, isoprene, nitrile rubber, polyacrylic rubber, silicone rubber, fluorosilicone rubber, perfluoroelastomers and ethylene-vinyl acetate (EVA). In other embodiments, the elastomeric layer 50 may include thermoplastic elastomers (TPE's), including but not limited to: thermoplastic rubbers, elastomeric alloys, thermoplastic polyurethanes, thermoplastic copolyesters, thermoplastic polyamides and polyolefin blends. Such materials have viscoelastic properties and when applied on the base fabric 20, allow the base fabric 20 to stretch or deform when a load acts on the base fabric 20 (e.g., due to the weight of a person sitting on a heated mattress etc.). Elastomers may allow the fabric heater 10 to stretch. In other words, the fabric heater 10 may develop a larger strain when a tensile load (e.g., body weight of a person sitting on a car seat) acts on the fabric heater 10, in comparison to inelastic polymers, such as PET plastic.

Embodiments of the fabric heater 10 may be exposed to a liquid during use. This may occur during surgery, and a heated blanket or a mattress with a fabric heater 10 such as those described elsewhere herein is provided to or beneath the patient. During or after surgery, liquids (e.g., water, hydrogen peroxide or urine) may contact the fabric heater 10. In such embodiments, the elastomeric layer 50 including elastomeric or thermoplastic elastomeric materials disclosed herein render the fabric heater 10 substantially liquid-resistant, thereby preventing a liquid (e.g., water, hydrogen peroxide, urine) from contacting at least one of the first and second faces 22, 24, on which the elastomeric layer 50 is applied. Such embodiments may facilitate protecting the fabric heater 10 from short term liquid exposure preventing damage and hotspot formation, thereby preventing accidental injury to the user. Fabric heaters with a liquid-proof elastomeric layer 50 do not require an outer liquid-proof protective shell, and may be covered with any material, including water permeable materials such as cloth or leather, for example in car seat heating applications.

In alternate embodiments, instead of or in addition to the elastomeric layer 50, the fabric heater 10 may be inserted into a liquid-proof shell of polymeric film. The polymeric film may be moisture resistant and can include an electrically insulating material. The polymer film may have elastic properties (e.g., modulus of elasticity, dynamic modulus etc.) that facilitate stretching (e.g., larger strain rate than rigid polymers such as PET). Exemplary materials for such polymeric film may include polyvinylidene chloride, polyurethane and the like. Similar plastic films are also within the scope of the invention. Such plastic films may be bonded or extruded on to the fabric heater 10. In such embodiments wherein the fabric heater 10 is inserted into the liquid-proof shell, the elastomeric layer 50 may be preferentially applied on to the base fabric 20, and the first and second electrical terminals 30, 40 may not be coated with the elastomeric layer 50.

While the elastomeric layer 50 or the liquid-proof shell may prevent short term exposure of the fabric heater 10 to liquids, such embodiments may not prevent a prolonged exposure to liquids. For instance, the outer liquid-proof shell may be damaged (e.g., due to hairline cracks) due to repetitive use, allowing water or other liquids such as urine or cleaning fluids to enter the shell and contact fabric heater 10. Once the liquid is inside the waterproof shell, it may not escape and the exposure of fabric heater 10 to the liquid may be prolonged. As mentioned elsewhere herein, an ingress of liquid could create risk of developing a hotspot. For example, if the outer liquid-proof shell is damaged, especially when used in medical applications, it may not be safe to continue to use the fabric heater 10. Alternatively, or in addition, the first and second electrical terminals 30, 40 may be exposed to a liquid. In such instances, to prevent the risk of developing hot spots, in some embodiments it may be beneficial to have the fabric heater 10 be permanently shut off from operation rather than continue to operate the fabric heater 10, with a hotspot that could cause a burn injury.

When a potentially dangerous condition due to liquid spill is detected, a shut-off condition is triggered to stop the fabric heater 10 from operating. Various embodiments allow fabric heater 10 to shut off operation of the fabric heater 10 as a result of prolonged contact with liquids. In some embodiments, the first and second electrical terminals 30, 40 (e.g., bus bars as shown in FIGS. 1-3) may contact the liquid such as where the base fabric 20 is not covered by the elastomeric layer 50. As the first and second electrical terminals 30, 40 may typically not contact the user, it may be beneficial to induce the failure to occur along the first or second electrical terminals 30, 40 to shut off when exposed to liquids. Additionally, various embodiments may cause a shut off to disable the heater relatively quickly, rather than allowing the fabric heater 10 to continue operation when it may fail unexpectedly, and/or cause an injury to a user.

FIGS. 1-3 illustrate the shutting off of the fabric heater 10 being accomplished by leaving a strip of fabric heater 10 along the first and second electrical terminals 30, 40, uncovered by the elastomeric elastomeric layer 50 that covers the rest of fabric heater 10 (shown in FIGS. 1-3). The strip of uncoated fabric heater 10 along the seams 60 of the first and second electrical terminals 30, 40 can be of a width in the range of approximately 0.1 inches to several inches. In an exemplary embodiment, the uncovered strip is approximately 0.5 inches wide. In another embodiment, it is approximately 0.1 inch wide. The first and second electrical terminals 30, 40 may be coupled to the fabric heater 10 at the strip of uncoated heater material.

Once a liquid is in contact with the uncoated strip of the fabric heater 10 near the seams 60 (shown in FIGS. 1-3) between the first and second electrical terminals 30, 40 and the base fabric 20, the fabric heater 10 may shut off operation as described below. If the fabric heater 10 is allowed to be in prolonged contact with a liquid, the liquid may be repelled by the elastomeric liquid-proof elastomeric layer 50 that covers the fabric heater 10. The fluid may, however, contact the fabric heater 10 along the uncoated strip at the seams 60. When the seams 60 or first and second electrical terminals 30, 40 are exposed to liquid, the heater material at the point of liquid contact may be damaged and it's electrical resistance increases to the point that the electrical current preferentially flow through the undamaged heater material adjacent the "dead spot." Excessive current may flow from the first and second electrical terminals 30, 40 into portions of the fabric heater 10 immediately adjacent the dead spot and in contact with the first or second electrical terminals 30, 40. With the excessive current flowing through a small area adjacent the dead spot, a very small area of the heater may begin heating to a temperature much higher than intended. This area may be referred to as a "hotspot". The hotspot may be less than 0.25 inches in diameter but may be preferably hot enough to melt the base fabric 20 of the heater at the hotspot. When the base fabric 20 melts at the edge of the dead spot and the first or second electrical terminals 30, 40, electrical conduction stops at that the hotspot. Thus, the excessive current flow may then move to the next area laterally along the electric terminal 30, 40 (e.g., the next stitch of conductive thread lateral to the melted spot) and the process may be repeated, further extending the size of the dead area of the heater. Eventually, the hotspot may travel along the seam of conductive thread coupling the first or second electrical terminals 30, 40 to the base fabric 20 until the ends of the first and second electrical terminals 30, 40 are reached. The first and second electrical terminals 30, 40 then become effectively electrically disconnected from the base fabric 20 and all current flow stops. At this point, the fabric heater 10 receives no further current flow, and shuts off its operation.

When the hotspot has progressed down the lengths of the first and second electrical terminals 30, 40, the fabric heater 10 shuts off operation, and prevents any accidental injury to a user. As the user rarely contacts the seams 60 and/or first and second electrical terminals 30, 40, the progression of the hotspot along the seam may minimally impact the user. Since the hotspot would be limited to a small area at any given time and the hotspot migrates along the first and second electrical terminals 30, 40 laterally towards the ends of the first and second electrical terminals 30, 40 rather than continuing to generate heat at a single location, a burn injury or a risk of fire is averted. This process acts like a thermal fuse, disabling a heater that has been exposed to damaging liquids or peroxide vapor, before it can injure the user.

Alternatively, to aid in shutting off the fabric heater 10 due to prolonged liquid exposure, the fabric heater 10 may be made of a material that melts at a lower temperature than the electrically conductive thread. For example, if the conductive thread is made of nylon with a melting temperature of 509° F. or polyester with a melting temperature of 500° F., it may be advantageous to choose a fabric heater 10 made of polypropylene with a melting temperature of 266-340° F. In this instance, the failure line in the heater material will follow the conductive thread along the electrical terminal.

Figure 5:
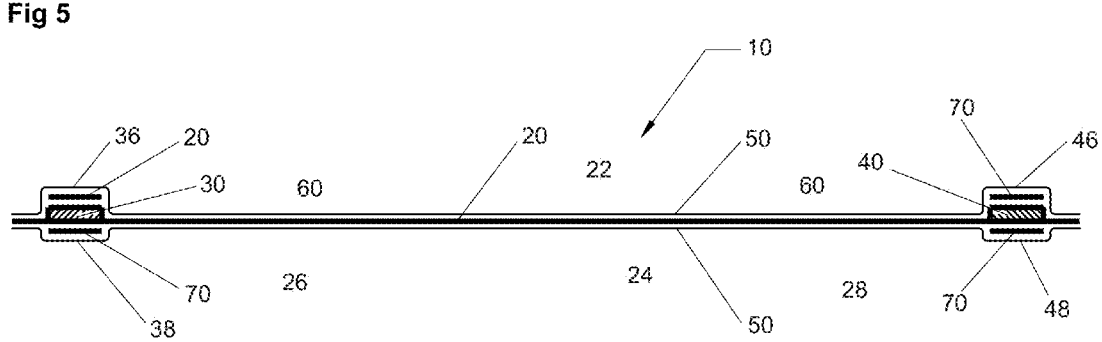
FIG. 5 is a front view of the fabric heater of FIG. 4 according to a second embodiment, with a first thermal layer applied on the electrical terminals and the elastomeric layer applied thereon.
Figure 6:
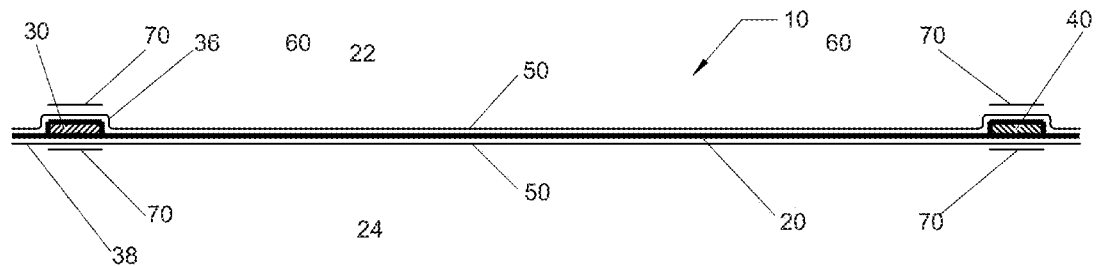
FIG. 6 is a front view of the fabric heater of FIG. 5, with the first thermal layer applied on the electrical terminals over the elastomeric layer.

Alternatively or in addition, as shown in FIGS. 5 and 6, a first thermal layer 70 may be applied proximate the first edge 26 and the second edge 28 to effectively contain any hotspots developing at the electrical terminal during a failure in the fabric heater 10. The first thermal layer 70 may cover the electrical coupling between the fabric heater 10 and the first and second electrical terminal 40. The first thermal layer 70 may have heat-resistant properties. As described elsewhere herein, the first and second electrical terminals 30, 40 may be sown together with the fabric heater 10 by an electrically conductive thread forming first and second seams 60. In such embodiments, the first and second seams 60 are covered by the first thermal layer 70. The first thermal layer 70 may create a thermal barrier over the first and second seams 60. Additionally, the first thermal layer 70 may be applied over the first and second electrical terminals 30, 40, to create a thermal barrier over the first and second electrical terminals 30, 40. Such embodiments may be useful for covering the small hotspot progressing along the first or second electrical terminals 30, 40 and for thermally insulating the hotspot from the user. The first thermal layer 70 may act as a tunnel and isolate the hotspot within the first thermal layer 70 that covers one or both sides of the seams 60 and/or first and second electrical terminals 30, 40. The user may thus be protected from progression of the hotspot along the seams 60 and/or first and second electrical terminals 30, 40.

As seen in FIG. 6, the first thermal layer 70 may be applied over the first and second electrical terminals 30, 40, and a elastomeric layer 50 or a polymeric shell may be provided over the first thermal layer 70. Alternatively, the elastomeric layer 50 extending from the surface of the fabric heater 10 may substantially enclose the first and second electrical terminals 30, 40 as shown in FIG. 5, and the first thermal layer 70 may be applied over the first and second electrical terminals 30, 40 on top of the elastomeric layer 50.

The first thermal layer 70 may include an elastomer having heat-resistant properties. In some embodiments, the elastomer is silicone rubber. The first thermal layer 70 may include a thermoplastic elastomer having heat-resistant properties. The first thermal layer 70 may include a heat-resistant fabric. The first thermal layer 70 may include a polymeric film. The first thermal layer 70 may include multiple layers of heat resistant materials. The heat resistant materials could also include heat resistant fabrics such as: Nomex, polyester, nylon, fiberglass or cotton. The heat resistant materials could also include heat resistant polymeric films such as Teflon (PTFE). It is anticipated that more than one of these materials may advantageously be used in combination to create a more effective thermal barrier over the first and second electrical terminals 30, 40 and/or the seams 60.

Certain embodiments of the fabric heaters described herein may provide one or more benefits. The fabric heaters according to certain embodiments retain their ability to deform into a compound curve because of their elastic properties. The fabric heater 10 may be exceptionally durable in comparison to laminate heaters due to the strength of the base fabric 20. Some embodiments of the heater may include an elastomeric coating, and may offer short-term protection from liquid exposure. Certain embodiments of the fabric heater 10 preferentially create and contain a small hotspot with limited heat production in the event of prolonged liquid exposure. Some embodiments also thermally insulate hotspots with excess current flow from the user to prevent burns. Such embodiments allow the fabric heater 10 to advantageously develop hotspot along the first and second electrical terminals 30, 40 and/or seams 60 where the hotspot progression can be controlled, predicted and accomplished relatively quickly, thereby allowing the fabric heater 10 to shut off safely when exposed to liquids for prolonged durations.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention.

What is claimed is:

1. A flexible heater, comprising:
   a flexible conductive base fabric extending from a first edge portion to a second edge portion opposite the first edge portion;
   a first electrical terminal extending along the first edge portion from a first end to a second end opposite the first end, the first electrical terminal electrically coupled to the base fabric at a first seam, the first seam including a stitched coupling of the first electrical terminal to the first edge portion with electrically conductive thread;
   a second electrical terminal extending along the second edge portion from a first end to a second end opposite the first end, the second electrical terminal electrically coupled to the base fabric at a second seam, the second seam including a stitched coupling of the second electrical terminal to the second edge portion with electrically conductive thread; and
   a first thermal layer applied proximate the first and second edge portions, the first thermal layer covering the first and second seams, the first thermal layer including a heat resistant elastomer, and
   wherein the semi-conductive polymer is polypyrrole.

2. The flexible heater of claim 1, wherein the first thermal layer that is proximate the first end portion is spaced apart from the first thermal layer that is proximate the second end portion.

3. The flexible heater of claim 1, wherein the first thermal layer includes a heat-resistant fabric.

4. The flexible heater of claim 1, wherein the first thermal layer is silicone rubber.

5. The flexible heater of claim 1, wherein the first thermal layer includes a thermoplastic elastomer.

6. The flexible heater of claim 1, the base fabric comprising a first face and second face opposite the first face, wherein at least one of the first and second faces is coated with a second coating that substantially covers an entire surface of at least one of the first and second faces, the second coating having liquid-resistant properties thereby preventing a liquid from contacting at least one of the first and second faces, on which the second coating is applied.

7. The flexible heater of claim 1, wherein the base fabric comprises 4-way stretch elastic fabric such that the base fabric may be stretched from a generally planar shape into a 3-dimensional compound curve and return to the generally planar shape.

8. The flexible heater of claim 7, wherein the base fabric includes a first face and a second face opposite the first face, wherein at least one of the first and second faces is coated with a second coating that substantially covers an entire surface of at least one of the first and second faces, the second coating having elastomeric and liquid-resistant properties to prevent a liquid from contacting at least one of the first and second faces while allowing the heater to maintain 4-way stretch elastic properties of the base fabric such that the heater is stretchable into a 3-dimensional compound curve.

9. The flexible heater of claim 1, wherein the base fabric melts at a lower temperature than the electrically conductive thread to provide predetermined failure paths in the base fabric along the first and second seams, wherein the predetermined failure path prevents a hotspot from occurring in the central portion of the base fabric in between the first and second electrical terminals, and the first thermal layer thermally insulates the predetermined failure path.

10. The flexible heater of claim 1, wherein the base fabric comprises a material having a melting point lower than its ignition temperature for burning.

11. The flexible heater of claim 1, further comprising a second coating that is an elastomeric layer applied on a first face and a second face of the first electrical terminal, and the first face and the second face of the second electrical terminal.

12. The flexible heater of claim 1, wherein the base fabric is a polymeric material.

13. The flexible heater of claim 1, wherein the base fabric is coated with a semi-conductive polymer.

14. The flexible heater of claim 1, further comprising a second coating, wherein the base fabric includes a first face and a second face opposite the first face and wherein at least one of the first and second faces is coated with the second coating, the second coating having elastomeric and liquid-resistant properties to prevent a liquid from contacting at least one of the first and second faces and wherein the second coating is an elastomeric layer extending from a first elastomeric layer end to a second elastomeric layer end,
wherein the first elastomeric layer end is disposed at a distance less than or equal to approximately 1 inch from the first electrical terminal, and
wherein the second elastomeric layer end is disposed at a distance less than or equal to approximately 1 inch from the second electrical terminal.

15. An elastic heater, comprising:
an elastic conductive base fabric extending from a first edge portion to a second edge portion opposite the first edge portion;
a first electrical terminal extending along the first edge portion from a first end to a second end opposite the first end, the first electrical terminal electrically coupled to the base fabric at a first seam, the first seam including a stitched coupling of the first electrical terminal to the first edge portion with electrically conductive thread;
a second electrical terminal extending along the second edge portion from a first end to a second end opposite the first end, the second electrical terminal electrically coupled to the base fabric at a second seam, the second seam including stitched coupling of the second electrical terminal to the second edge portion with electrically conductive thread; and
a first thermal layer applied proximate the first and second edge portions, the first thermal layer covering the first and second seams, the first thermal layer including a thermally insulative elastomer,
wherein a predetermined failure path is provided in the base fabric along the first and second seams, and wherein the predetermined failure path provides a heater that is configured, in the event of a failure of the base fabric, to fail along a predetermined failure path, and
wherein the first thermal layer is configured to thermally insulate a patient from the predetermined failure path.

16. The elastic heater of claim 15, wherein the first thermal layer includes a thermoplastic elastomer.

17. The flexible heater of claim 15, wherein the first thermal layer proximate the first end portion is spaced apart from the first thermal layer proximate the second end portion.

18. An elastic heater, comprising:
a elastic conductive base fabric extending from a first edge portion to a second edge portion opposite the first edge portion, the base fabric having a first face and a second face opposite the first face;
a first electrical terminal extending along the first edge portion from a first end to a second end opposite the first end, the first electrical terminal electrically coupled to the base fabric at a first seam, the first seam including a stitched coupling of the first electrical terminal to the first edge portion with electrically conductive thread;
a second electrical terminal extending along the second edge portion from a first end to a second end opposite the first end, the second electrical terminal electrically coupled to the base fabric at a second seam, the second seam including stitched coupling of the second electrical terminal to the second edge portion with electrically conductive thread; and
a first thermal layer applied proximate the first and second edge portions, the first thermal layer covering the first and second seams, the first thermal layer including a thermally insulative elastomer,
wherein the base fabric melts at a lower temperature than the electrically conductive thread to provide predetermined failure paths in the base fabric along the first and second seams, and wherein in the event of a failure of the base fabric, the predetermined failure path prevents a hotspot from occurring in the central portion of the base fabric in between the first and second electrical terminals, and wherein the first thermal layer provides a heater configured to thermally insulate a patient from the predetermined failure path.

19. The elastic heater of claim 18, wherein the first thermal layer includes a thermoplastic elastomer.

20. The flexible heater of claim 18, wherein the first thermal layer proximate the first end portion is spaced apart from the first thermal layer proximate the second end portion.

* * * * *